United States Patent [19]

Neuwirth

[11] 3,996,921
[45] Dec. 14, 1976

[54] METHOD AND APPARATUS FOR ENDOSCOPY

[75] Inventor: Robert S. Neuwirth, Bronx, N.Y.

[73] Assignee: Pharmacia Inc., Piscataway, N.J.

[22] Filed: Apr. 17, 1975

[21] Appl. No.: 569,067

[52] U.S. Cl. .......................... 128/2 R; 128/2.05 C; 128/4

[51] Int. Cl.² ........................................... A61B 1/00

[58] Field of Search ...................... 128/1, 2, 2.05, 4

[56] References Cited
UNITED STATES PATENTS

| | | | |
|---|---|---|---|
| 3,313,292 | 4/1967 | Cook | 128/2 S |
| 3,674,010 | 7/1972 | Falenks | 128/2 R |
| 3,882,852 | 5/1975 | Sinnreich | 128/4 |

*Primary Examiner*—Delbert B. Lowe
*Attorney, Agent, or Firm*—Hubbell, Cohen, Stiefel & Gross

[57] ABSTRACT

A method and apparatus for use in endoscopic examination of a hollow internal organ, such as hysteroscopic examination of the uterus, includes an inflatable cuff for infusing a pressurized viscous fluid into the interior of the uterine cavity for minimizing distortion of an image of the organ interior viewable through the endoscope. The viscous fluid is an optically clear innocuous liquid having a predetermined viscosity such as between 130 and 300 centistokes at 20° C, and a predetermined optical density, such as a refractive index of 1.3912 at 21° C. This viscous fluid is contained in a self-contained sterile packet reservoir which is removably retained within the inflatable cuff with the viscous fluid being pressurized and released from the reservoir into the endoscope to be infused into the organ interior under the controlled pressure of the inflated cuff surrounding the fluid reservoir packet.

26 Claims, 2 Drawing Figures

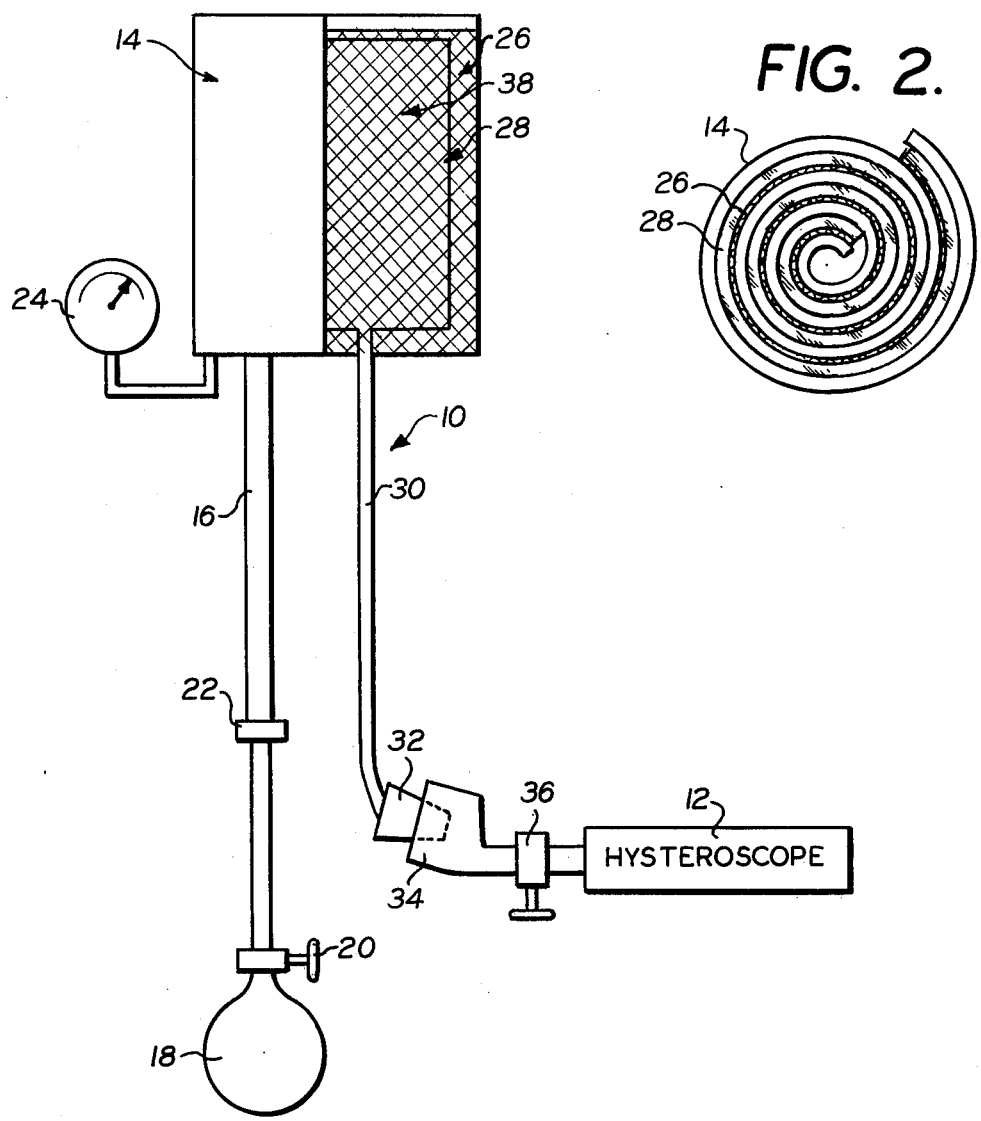

METHOD AND APPARATUS FOR ENDOSCOPY

BACKGROUND OF THE INVENTION

1. Field of the Invention

The present invention relates to a method and apparatus for infusing a pressurized viscous fluid, such as for use in endoscopy.

2. Description of the Prior Art

The use of fluids, particularly water, saline or air in examinations of hollow internal organs, such as in conjunction with cystoscopes, proctoscopes and gastroscopes, is well known. In addition, the use of such fluids via an endoscope to distend an internal organ for improved viewing of the organ is also known in the prior art. Examples of prior art systems for directly introducing pressurized air, or a fluid such as water or saline, into an internal organ for endoscopic examination thereof are illustrated in U.S. Pat. Nos. 1,345,406 and 2,236,842. Other examples of elaborate prior art valving arrangements for introducing fluid into a hollow organ to inflate the organ are disclosed in U.S. Pat. Nos. 1,741,740; 1,453,975; 3,570,448 and 3,239,074. In addition, the concept of an inflatable pressurized cuff for transferring pressure from the inflatable cuff to provide a pressure infusor, is well known, such as, by way of example, the type of pressure infuser available from Fenwal Labs under designation no. FT123, as well as, by way of example, the type of pressurized cuffs disclosed in U.S. Pat. Nos. 3,468,308; 3,228,395; Re. 26,006 and 3,054,401. None of the prior art known to applicant employed a viscous fluid for minimizing distortion of an image of the interior of the organ viewable through an endoscope which flowed sufficiently freely at room temperature to enable it to readily be used quickly enough in order to inflate the uterus so that all parts of it can be viewed while simultaneously not distoring images viewed through the hysteroscope. Previously, in utilizing this viscous fluid, it had to be withdrawn into a sterile syringe which was then attached to sterile tubing and forced into the hysteroscope thereby requiring more than one person to accomplish the hysteroscopic examination of the patient; one person being required to control the infusion of the viscous fluid into the uterine cavity through the hysteroscope and another person being required to actually accomplish the hysteroscopic examination. These disadvantages of the prior art are overcome by the present invention.

SUMMARY OF THE INVENTION

A method and apparatus for endoscopic examination of a hollow internal organ through infusion of a pressurized viscous fluid into the interior of the organ under the controlled pressure of an inflated surrounding cuff, wherein the fluid minimizes distortion of an image of the organ interior viewable through an endoscope, are provided. The fluid infusing means comprises an inflatable circumferential cuff, a self-contained sterile packet reservoir for the viscous fluid, which fluid is an optically clear innocuous liquid having a predetermined viscosity and a predetermined optical density, with the cuff comprising means, such as a mesh pocket within the inner surface of the cuff, for removably retaining the packet, and means such as a hand operable air bulb for controllably inflating the surrounding cuff to a pressure sufficient to cause the viscous fluid to be pressurized and released from the surrounded packet reservoir into a dispensing channel and be infused into the organ interior through an endoscope under the controlled pressure of the inflated surrounding cuff. This method and apparatus may particularly be utilized for hysteroscopy for viewing the interior of the uterus and the viscous fluid, in such an instance, preferably has a viscosity range of between 130 and 300 centistokes at 20° C and an optical density of substantially 1.3912 at 21° C. Furthermore, the viscous fluid preferably comprises a viscous aqueous solution of 15 to 45% by weight of dextran and 5 to 20% by weight of an additive selected from the group consisting of a monosaccharide, an oligosaccharide and a sugar alcohol.

BRIEF DESCRIPTION OF THE DRAWINGS

FIG. 1 is a diagrammatic illustration of the preferred embodiment of the apparatus of the present invention; and FIG. 2 is a plan view of the inflatable cuff portion of the apparatus shown in FIG. 1 with the sterile packet in place during normal use of the apparatus.

DETAILED DESCRIPTION OF THE PREFERRED EMBODIMENT

Referring now to the drawings in detail, and initially to FIG. 1 thereof, the apparatus of the present invention is preferably utilized in endoscopic examination of a hollow internal organ and, as presently preferred, is for hysteroscopic examination of the uterine cavity, although any other type of endoscopic examination of any other internal organ of the body may be accomplished without departing from the present invention. For purposes of explanation, the invention will be described in terms of the presently preferred utilization for hysteroscopic examination of the uterine cavity. Accordingly, as shown and preferred in FIG. 1, a conventional hysteroscope 12 is provided for use with the apparatus of the present invention, generally referred to by the reference numeral 10. The apparatus 10 preferably includes a conventional inflatable cuff 14, which is preferably air inflatable by means of a conventional rubber hose 16 connection to a conventional hand operable air bulb or hand pump 18. Conventional valves 20 and 22 are associated with air pump 18 and inflatable cuff 14 for controllably regulating the pressure within inflatable cuff 14 in conventional fashion, such as by closing the valves 20 and 22 when the desired pressure has been reached within cuff 14, thereby maintaining the pressure within cuff 14. A conventional pressure gauge 24 is associated with inflatable cuff 14 to monitor the pressure therein and conventionally provide a substantially instantaneous display of this pressure value so that the user can determine when the desired pressure within the cuff 14 has been reached, as well as to monitor the dynamic pressure within the cuff throughout its use in the endoscopic examination of the hollow internal organ. As also shown and preferred in FIGS. 1 and 2, the inflatable cuff 14 includes a mesh pocket 26 secured to the inner surface of the cuff 14 as the cuff is rolled up, as shown in FIG. 2, which pocket 26 is preferably open at the top thereof for removably retaining a sterile packet, such as a conventional plastic transfer bag 28, therein. The mesh pocket 26 may preferably be formed of nylon netting. As also shown and preferred in FIG. 1, the sterile packet or transfer bag 28, which, as will be described in greater detail hereinafter, forms a reservoir for a preferred viscous fluid, which is preferably an optically clear innocuous liquid having a predetermined viscosity and a predetermined optical density to be described in greater detail hereinafter, includes a dispensing channel, such as a conventional plastic tube 30 extending therefrom which preferably terminates in a dispensing nipple 32. The nipple 32 preferably provides a friction fit within a connector 34 which is in flow through communication with the hysteroscope 12. The connector 34 may conventionally be provided as a portion of the hysteroscope or as a separate coupling element insertable in the hysteroscope 12. Coupling element 34, as shown and preferred, preferably includes a conventional valve 36, such as a thread needle valve, for regulating the flow of infusate into the hysteroscope 12 from reservoir 28. As shown and preferred in FIG. 2, and as will be described in greater detail hereinafter in discussing the preferred method of the present invention, the sterile packet 28 is preferably inserted within the mesh pocket 26 and the inflatable cuff 14 is rolled up to circumferentially surround the packet 28 in the manner illustrated in FIG. 2.

With respect to the preferred viscous fluid for use with the apparatus 10 of the present invention, this fluid is preferably an optically clear innocuous liquid preferably having a viscosity range of between 130 and 300 centistokes at 20° C and a preferred optical density or refractive index of 1.3912 at 21° C when such fluid is to be utilized for hysteroscopic examination of the uterine cavity. Generally, the viscosity of the fluid 38 contained in the reservoir or packet 28 may be varied, depending on which body cavity it is intended to examine, the viscosity being controlled by varying the dextran content by selecting dextrans having different average molecular weights. Thus, viscosity values between about 50 and 400 and preferably 100 to 350 centistokes may be utilized for hysteroscopy; with the viscosity range for hysteroscopy preferably being between 130 and 300 centistokes at 20° C. Furthermore, most preferably, the viscous fluid 38 has a viscosity of about 260 centistokes at 20° C and about 225 centistokes at 37° C, with the preferred optical density about 1.3912, at 21° C, for use with the apparatus 10 in the present invention to accomplish hysteroscopic examination of the uterine cavity. In addition, the viscous fluid 38 is preferably a viscous aqueous solution of 15 to 45% by weight of a dextran, such as one having an average molecular weight of 10,000 to 200,000, which contains an additive of from 5 to 20° C by weight of a monosaccharide, such as glucose or fructose, an oligosaccharide, such as invert sugar, maltose or saccharose, or a sugar alcohol, such as sorbitol or mannitol.

In utilizing the apparatus 10 of the present invention to practice the preferred method of the present invention, the preferred viscous fluid 38 does not normally flow sufficiently freely at room temperature to enable it to be used quickly in the absence of pressurization thereof. The viscous fluid 38 is normally instilled into the uterine cavity, in the case of hysteroscopy of the uterine cavity, through the conventional hysteroscope 12 where it serves to inflate the uterus so that all parts of it can be viewed as well as to minimize distortion of images of the interior of the uterine cavity viewed through the hysteroscope 12. The sterile packet 28 is preferably a pliable plastic bag which, as previously mentioned, is inserted in the mesh pocket 26 of the cuff 14. The cuff 14 is then rolled up to circumferentially surround the sterile packet 28 in the manner illustrated in FIG. 2 with the dispensing channel 30 extending therefrom into coupling 34 through nipple 32 to provide a flow through channel from the reservoir packet 28, through tube 30, through nipple 32, through coupling 34 and valve 36 and therefrom, through hysteroscope 12, in conventional fashion, into the interior of the uterine cavity where it serves to inflate the uterus. The inflatable cuff 14 is preferably a manometric device which functions in a manner similar to a syphgmomanometer in that it is preferably inflated by squeezing the air bulb 18 in a pumping fashion until the desired pressure is displayed on pressure gauge 24 which displays the pressure to which the cuff 14 is inflated, the pressure, by way of example, being registered in millimeters of mercury. In conventional fashion, the pressure in inflatable cuff 14 is transferred from the cuff 14 to the pliable plastic packet 28 which serves as the reservoir for the viscous fluid 38. When the pressure on the bag or reservoir 28 which contains the viscous fluid due to the inflatable cuff 14 is greater than the pressure opposing it, the viscous fluid contained in bag 28 will be forced through dispensing channel 30 and nipple 32 into coupling member 34 and, through valve 36 and hysteroscope 12, into the uterine cavity. The desired pressure is the flow pressure required to cause the viscous fluid to be forced from its reservoir in a free flow to the hysteroscope 12, such as, by way of example, a presure of up to 150 millimeters of mercury at 25° C for the preferred viscous fluid described above having a preferred optical density of 1.3912 at 21° C and a preferred viscosity of 260 centistokes at 20° C and 225 centistokes at 37° C. The valve 36 preferably controls the flow rate of the viscous fluid 38 through the hysteroscope 12. Thus, by means of the apparatus 10 of the present invention, the cuff 14 surrounding the packet 28 containing the viscous fluid reservoir 38 may be controllably inflated to a pressure sufficient to cause the viscous fluid 38 to be pressurized and thereby released from the reservoir 28 into the dispensing channel 30 and be infused into the organ interior through the hysteroscope 12 under the controlled pressure of the inflated surrounding cuff 14.

By utilizing the apparatus and method of the present invention endoscopic examination of the interior of a hollow internal organ, such as the uterus, may readily be accomplished by a single person utilizing a viscous optically clear, innocuous liquid which inflates the organ so that all parts of it can be viewed and minimizes distortion of images viewed through the endoscope, by supplying the viscous fluid to the endoscope from a removably insertable sterile packet reservoir for the fluid under the controlled pressure of an inflated surrounding cuff.

What is claimed is:

1. An apparatus for use in endoscopic examination of a hollow internal organ comprising an endoscope for viewing the interior of said organ; and means operatively connected to said endoscope for infusng a presurized viscous fluid into the interior of said organ through said endoscope for minimizing distortion of an image of said organ interior viewable through said endoscope, said infusing means comprising an inflatable circumferential cuff, a self-contained sterile packet reservoir for said viscous fluid, said viscous fluid being an optically clear innocuous liquid having a predetermined viscosity and a predetermined optical density dependent on said organ to be endoscopically examined, said cuff comprising means for removably retaining said packet, said retained packet being circumferentially surrounded by said cuff and comprising means in communication with said endoscope for enabling flow of said pressurized viscous fluid therethrough to said endoscope; and means for controllably inflating said surrounding cuff to a presure sufficient to cause said viscous fluid to be pressurized and released from said surrounded packet reservoir into said communication means and be infused into said organ interior through said endoscope under the controlled pressure of said inflated surrounding cuff.

2. An apparatus in accordance with claim 1 wherein said endoscope comprises a hysteroscope for viewing the interior of the uterus organ, and said cuff inflating means comprises a hand operable air bulb for air inflating said cuff to said sufficient pressure to pressurize said fluid and release said pressurized fluid from said reservoir into said communication means and be infused into the uterine cavity interior under the controlled pressure of said air inflated surrounding cuff.

3. An apparatus in accordance with claim 2 wherein said viscous fluid has a viscosity range of between 50 and 400 centistokes.

4. An apparatus in accordance with claim 3 wherein said viscous fluid has a viscosity range of between 100 and 350 centistokes.

5. An apparatus in accordance with claim 4 wherein said viscous fluid has a viscosity range of between 130 and 300 centistokes at 20° C.

6. An apparatus in accordance with claim 5 wherein said viscous fluid has a viscosity of substantially 260 centistokes at 20° C.

7. An apparatus in accordance with claim 5 wherein said viscous fluid has a viscosity of substantially 225 centistokes at 37° C.

8. An apparatus in accordance with claim 2 wherein said viscous fluid has an optical density of substantially 1.39 at 21° C.

9. An apparatus in accordance with claim 8 wherein said viscous fluid has a viscosity of substantially 260 centistokes at 20° C.

10. An apparatus in accordance with claim 8 wherein said viscous fluid has a viscosity of substantially 225 centistokes at 37° C.

11. An apparatus in accordance with claim 1 wherein said means for removably retaining said packet comprises a mesh pocket secured to the interior surface of said cuff, said packet being removably insertable in said mesh pocket.

12. An apparatus in accordance with claim 2 wherein said viscous fluid comprises a viscous aqueous solution of 15 to 45% by weight of dextran and 5 to 20% by weight of an additive selected from the group consisting of a monosaccharide, an oligosaccharide and a sugar alcohol.

13. An apparatus for enabling infusion of a pressurized viscous fluid comprising an inflatable circumferential cuff, a self-contained sterile packet reservoir for said viscous fluid, said viscous fluid being an innocuous liquid having a predetermined viscosity and a predetermined optical density dependent on the intended use of said infused pressurized viscous fluid, said cuff comprising means for removably retaining said packet, said retained packet being circumferentially surrounded by said cuff and comprising dispensing means for enabling flow of said pressurized viscous fluid therethrough from said reservoir; and means for controllably inflating said surrounding cuff to a pressure sufficient to cause said viscous fluid to be pressurized and released from surrounded packet reservoir into said dispensing means and be infused therefrom under the controlled pressure of said inflated surrounding cuff.

14. An apparatus in accordance with claim 13 wherein said cuff inflating means comprises a hand operable air bulb for air inflating said cuff to said sufficient pressure to pressurize said fluid and release said pressurized fluid from said reservoir into said dispensing means and be infused therefrom under the controlled pressure of said inflated surrounding cuff.

15. An apparatus in accordance with claim 13 wherein said means for removably retaining said packet comprises a mesh pocket secured to the interior surface of said cuff, said packet being removably insertable in said mesh pocket.

16. In a method for edoscopically examining the interior of a hollow internal organ in which the organ is inflated with a fluid to assist in visual internal endoscopic examination of said organ, the improvement comprising the step of inflating said organ by infusing a pressurized viscous fluid into the interior of said organ for minimizing distortion of an edoscopically viewable image of said organ interior, said viscous fluid being an optically clear innocuous liquid having a predetermined viscosity and a predetermined optical density dependent on said organ to be endoscopically examined, said infusing step comprising the steps of placing a sterile packet reservoir of said fluid in an inflatable surrounding cuff, and controllably inflating said surrounding cuff to a pressure sufficient to cause said viscous fluid to be pressurized and released from said surrounded packet reservoir and be infused into said organ interior under the controlled pressure of said inflated surrounding cuff.

17. A method in accordance with claim 16 wherein said inflating step comprises inflating the uterus organ by infusing said pressurized viscous fluid into the uterine cavity interior under the controlled pressure of said inflated surrounding cuff.

18. A method in accordance with claim 17 wherein said viscous fluid has a viscosity range of between 50 and 400 centistokes.

19. A method in accordance with claim 18 wherein said viscous fluid has a viscosity range of between 100 and 350 centistokes.

20. A method in accordance with claim 19 wherein said viscous fluid has a viscosity range of between 130 and 300 centistokes at 20° C.

21. A method in accordance with claim 20 wherein said viscous fluid has a viscosity of substantially 260 centistokes at 20° C.

22. A method in accordance with claim 20 wherein said viscous fluid has a viscosity of substantially 225 centistokes at 37° C.

23. A method in accordance with claim 17 wherein said viscous fluid has an optical density of substantially 1.39 at 21° C.

24. A method in accordance with claim 23 wherein said viscous fluid has a viscosity of substantially 260 centistokes at 20° C.

25. A method in accordance with claim 23 wherein said viscous fluid has a viscosity of substantially 225 centistokes at 37° C.

26. A method in accordance with claim 17 wherein said viscous fluid comprises a viscous aqueous solution of 15 to 45% by weight of dextran and 5 to 20% by weight of an additive selected from the group consisting of a monosaccharide, an oligosaccharide and a sugar alcohol.

* * * * *